US005284689A

United States Patent [19]
[11] Patent Number: 5,284,689

Laurash et al.
[45] Date of Patent: Feb. 8, 1994

[54] PRODUCT LABEL ASSEMBLY

[75] Inventors: David F. Laurash, Bellbrook; Rajendra Mehta, Centerville; Gary W. Doll, Englewood, all of Ohio

[73] Assignee: The Standard Register Company, Dayton, Ohio

[21] Appl. No.: 944,490

[22] Filed: Sep. 14, 1992

[51] Int. Cl.⁵ .................... A61F 13/02; G09F 15/02

[52] U.S. Cl. .................... 428/40; 428/41; 428/42; 428/43; 428/194; 428/195; 428/202; 428/212; 428/214; 428/354; 428/355; 428/914; 283/81

[58] Field of Search .................... 428/40-43, 428/194, 195, 202, 914, 354, 212, 214, 355; 283/81

[56] References Cited

U.S. PATENT DOCUMENTS

| | | | |
|---|---|---|---|
| 3,313,121 | 5/1968 | Singer | 282/28 |
| 3,565,463 | 2/1971 | Taylor | 283/10 |
| 4,029,341 | 6/1977 | Neill et al. | 283/21 |
| 4,204,706 | 5/1980 | Blum et al. | 283/21 |
| 4,250,216 | 2/1981 | Janssen | 428/78 |
| 4,277,089 | 7/1981 | Lockhart | 283/21 |
| 4,347,274 | 8/1982 | Janssen | 428/78 |
| 4,460,634 | 7/1984 | Hasegawa | 428/124 |
| 4,479,838 | 10/1984 | Dunsirn et al. | 156/247 |
| 4,654,251 | 3/1987 | Okada et al. | 428/202 |
| 4,747,619 | 5/1988 | Sager | 283/81 |
| 4,833,122 | 5/1989 | Doll et al. | 428/40 |
| 4,889,234 | 12/1989 | Sorensen | 428/40 |
| 4,900,597 | 2/1990 | Kurtin | 428/41 |
| 4,940,690 | 7/1990 | Skees | 428/41 |
| 4,995,641 | 2/1991 | Landry | 428/202 |
| 5,039,652 | 8/1991 | Doll et al. | 428/195 |

*Primary Examiner*—Henry F. Epstein
*Assistant Examiner*—Nasser Ahmad
*Attorney, Agent, or Firm*—Killworth, Gottman, Hagan & Schaeff

[57] ABSTRACT

A printable product label assembly having a selectably adhesive portion is provided. The label assembly includes a printable face sheet overlying a liner sheet, a releasable adhesive securing a first portion of the face sheet to a first portion of the liner sheet such that the face sheet and liner sheet are readily separable upon the application of a sufficient delaminating force. A pressure sensitive adhesive secures a second portion of the face sheet to a second portion of the liner sheet such that when the label is removed from the liner sheet, only a selected area of the label includes the pressure sensitive adhesive, while the remainder of the label is nontacky to the touch.

10 Claims, 4 Drawing Sheets

PRODUCT LABEL ASSEMBLY

BACKGROUND OF THE INVENTION

This invention relates to a product label assembly, and more particularly to a printable product label comprising a face sheet and liner sheet which are adhered together by a combination of releasable and pressure sensitive adhesives on selected portions of the label.

Numerous businesses produce a wide variety of labels, nameplates, identification cards, tags, forms, and the like in large quantities. Such products typically have nonvariable information (i.e., information which is the same for the entire printing run of the product) printed thereon by high speed printing devices. It is desirable to produce such products on a continuous web, with individual labels, forms, or the like being adhesively attached to the web. Variable information, such as names, addresses, prices, etc., may be printed at the same time, or in a later printing step.

With the proliferation of computer-operated printers, including both impact and nonimpact printers, one recent trend has been for the customer to purchase labels and add variable information to the labels using the customer's own printing equipment. This permits the customer to print on his own schedule, and not be dependent upon an outside printing house. For example, for supermarkets running special sales prices on a variety of items on a weekly basis, deadlines to provide advertising and in-store labels and displays are very short.

Pressure sensitive adhesives have been utilized to secure the product to a continuous web during printing. Typically, labels or the like are attached to a release liner by a pressure sensitive adhesive. When the pressure sensitive adhesive label is removed from the release liner, the label is attached to another surface by means of the tacky adhesive backing on the label.

However, in some instances, it has been desirable to have both surfaces of a label as well as the surface of the web from which the label is released to be clean and non-tacky. Such labels utilize clean release or fugitive adhesives. These releasable adhesives exhibit cohesive failure instead of the usual adhesive failure exhibited by typical pressure sensitive adhesives. These releasable adhesives are compositions which form relatively weak bonds but which adhere well to paper and other surfaces. Failure occurs within the releasable adhesive film itself when a layer of a laminate is subjected to peeling forces. When cohesive failure occurs in such releasable adhesives, a thin film of adhesive remains on the back surface of the face sheet, on the surface of the liner sheet, or both. However, the film does not exhibit tack and has no adverse effect on the appearance or handling characteristics of the product. Moreover, the surface can be readily printed on.

For example, Dunsirn et al, U.S. Pat. No. 4,479,838, teaches a coupon structure which is removably attached to a base sheet on a product by a non-tacky adhesive so that when the coupon is removed, neither the coupon nor the base sheet have a tacky surface.

While releasable adhesives are useful, in some instances, it is desirable to have a product label which has a tacky, pressure-sensitive adhesive on only a portion of the back of the label. For example, a tacky portion of product pricing and advertising labels may be adhered to the shelves holding the products in a supermarket, discount store, hardware store or other business. Current methods of producing such tag or label products typically use face stock laminated to a release liner with pressure sensitive adhesive. During the converting process, the liner sheet is die cut from the back so that when the individual label is removed from the liner, a portion of the liner material remains with the face stock to render that area from sticking.

However, the liner material is easily removed from the label back, defeating the purpose of having non-tacky areas on the label back. Moreover, die cutting of the label from the back adds to production costs and may cause problems in the converting process. Die cutting of the liner may also weaken the structure of the label product which causes numerous problems if the label must be later processed through additional printers to add variable information. Such problems are particularly common where nonimpact printers such as laser printers are used. The path the label takes through such printers may include many U- or S-shaped turns which may cause the label face sheet and liner to delaminate prematurely, jamming the printer. Passing the labels through hot fuser rolls to fuse toner to the label face may also contribute to premature delamination. In addition, the liner may get caught on other internal parts of the printer, causing jamming of the printer.

Accordingly, the need still exists in the art for a product label which can provide a combination of tacky and nontacky adhesives on selected portions of a tag, label, or advertisement, which avoids the need for die cutting the liner sheet, which may be later printed with variable information, and which reduces or eliminates premature liner separation problems.

SUMMARY OF THE INVENTION

The present invention meets that need by providing a product label, tag, or advertising hang piece comprising a face sheet and liner sheet which incorporates both a pressure sensitive adhesive and a releasable adhesive on selected portions thereof. The face sheet can be readily peeled from the liner and used as a label, tag, or the like in which only a selected area of the label includes a pressure sensitive adhesive for adhering the label to a substrate while the remainder of the label remains non-tacky.

In accordance with one aspect of the invention, a printable product label assembly having a selectably adhesive portion is provided which comprises a liner sheet and a printable face sheet overlying the liner sheet. A releasable adhesive secures a first portion of the surface of the face sheet to a first portion of the surface of the liner sheet such that the face sheet and liner sheet are readily separable upon the application of a sufficient delaminating force. A pressure sensitive adhesive secures a second portion of the surface of the face sheet to a second portion of the surface of the liner sheet. A portion of the surface of the liner sheet which is substantially coextensive with the pressure sensitive material includes a coating of a release material. Preferably, the area of the liner sheet containing the release material extends beyond the area of the face sheet containing the pressure sensitive adhesive to ensure proper separation of the label from the liner.

The portions of the liner and face sheets secured together by the releasable adhesive and the pressure sensitive adhesive are preferably non-coextensive (i.e., they do not overlap). Further, it is not necessary that the pressure sensitive adhesive or the releasable adhesive cover the entire area of the label. The releasable adhesive may be applied to form a pattern on selected portions of the face sheet or liner sheet, with pressure sensitive adhesive being applied to other portions of the face sheet or liner sheet. For example, the releasable adhesive may be coated on the liner sheet in a striped pattern.

In a further embodiment of the invention, the interface between the liner sheet and face sheet contains means for forming an image on either or both surfaces of the liner sheet and face sheet. Such means comprises a color former composition which, when exposed to a color developer composition, forms a distinctive color. At least one of the compositions is preferably contained in a plurality of capsules which rupture upon the application of an imaging force on the face sheet. Preferably, the surface of the liner sheet contains the color developer composition. When an imaging force is applied to the face sheet, the capsules of the color former composition are ruptured and mix with the color developer composition on the surface of the liner sheet to form a distinctive color, duplicating the information from the imaging force on the liner sheet.

In an alternative embodiment of the invention, the color developer composition and color former composition are blended together and coated on the surface of the liner sheet, with at least one of the compositions being encapsulated. When the color former composition is exposed to the color developer composition, a distinctive color is formed on the liner sheet. In another alternative embodiment, the color developer composition is coated on either or both surfaces of the liner sheet and face sheet, while the color former composition is contained in capsules dispersed in the adhesive.

In yet another embodiment of the invention, the printable product label assembly comprises a liner sheet and a printable face sheet overlying the liner sheet in which a pressure sensitive adhesive secures a portion of the surface of the face sheet to a portion of the surface of the liner sheet. A portion of the surface of the face sheet which is substantially coextensive with the pressure sensitive material includes a coating of release material. Preferably, the release material is pattern coated on the face sheet and the pressure sensitive adhesive is coated over the release material so that when the liner sheet is removed, the pressure sensitive adhesive stays on the liner, leaving the back of the face sheet tack free.

In yet another embodiment of the invention, the product label assembly comprises a printable liner sheet and a printable face sheet overlying the liner sheet. A pressure sensitive adhesive secures a first portion of the surface of the face sheet to a first portion of the surface of the liner sheet. A second portion of the surface of the face sheet and the liner sheet includes a coating of a release material. The portion of the face sheet containing the release material is laminated to the portion of the liner sheet containing the pressure sensitive adhesive, and the portion of the face sheet containing the pressure sensitive adhesive is laminated to the portion of the liner sheet containing the release material. Both the face sheet and liner sheet may be printed with variable information. When separated, the face sheet and liner sheet form two labels, each having the pressure sensitive adhesive on a portion thereof. In a preferred form, the face sheet of the label assembly is die cut to form a plurality of labels. The labels are preferably produced from a continuous web to facilitate printing and handling by automated equipment. The continuous web of labels is preferably defined by perforated lines and folded zig-zag into a stack.

In practice, the product label may be assembled and preprinted with nonvariable product information. In addition, various combinations of color former and color developer compositions may be coated onto continuous webs of the face sheet and/or liner sheet or incorporated into the releasable adhesive composition. Variable information, such as item names and pricing information may then be added by the end user on site by passing the label web assembly, or individual label sheets, through a printer. The combination of the uncut supporting liner and releasable and pressure sensitive adhesives securing the face and liner sheets together prevent premature delamination of the assembly.

Accordingly, it is an object of the present invention to provide a printable product label assembly comprising a face sheet and a liner sheet having a selectably tacky adhesive portion utilizing in combination a pressure sensitive and/or a releasable adhesive. It is a further object of the present invention to provided such a printable product label assembly which avoids the need to die-cut the supporting liner sheet. It is yet a further object of the present invention to provide such a product label assembly which can be printed on site by an end user with variable information. These, and other objects and advantages of the invention will become apparent from the following detailed description, the accompanying drawings, and the appended claims.

Figure 9:
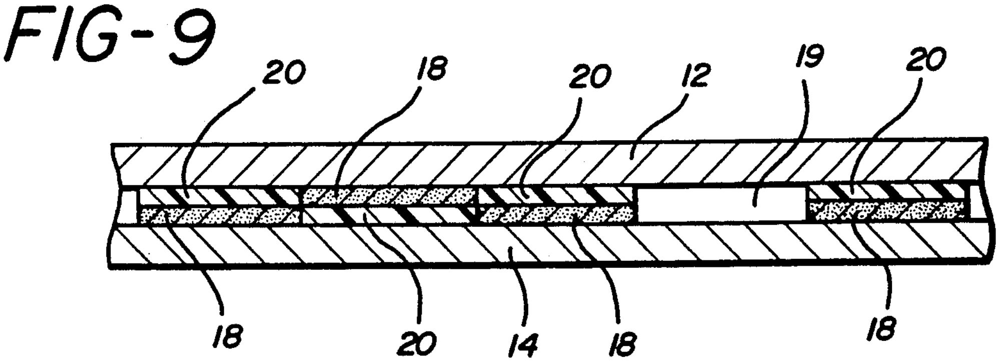
Figure 10:
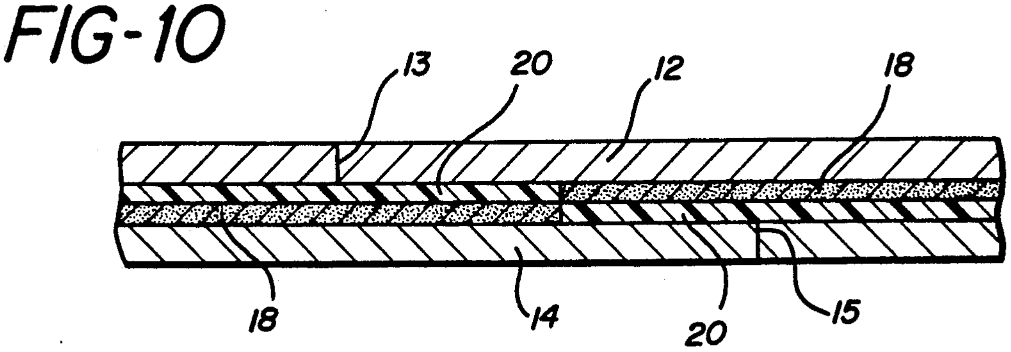

FIG, 8 is a fragmentary sectional view of another embodiment of the label assembly of the present invention;

FIG. 9 is a fragmentary sectional view of another embodiment of the label assembly of the present invention; and FIG. 10 is a fragmentary sectional view of another embodiment of the label assembly of the present invention.

DESCRIPTION OF THE PREFERRED EMBODIMENTS

Figure 1:
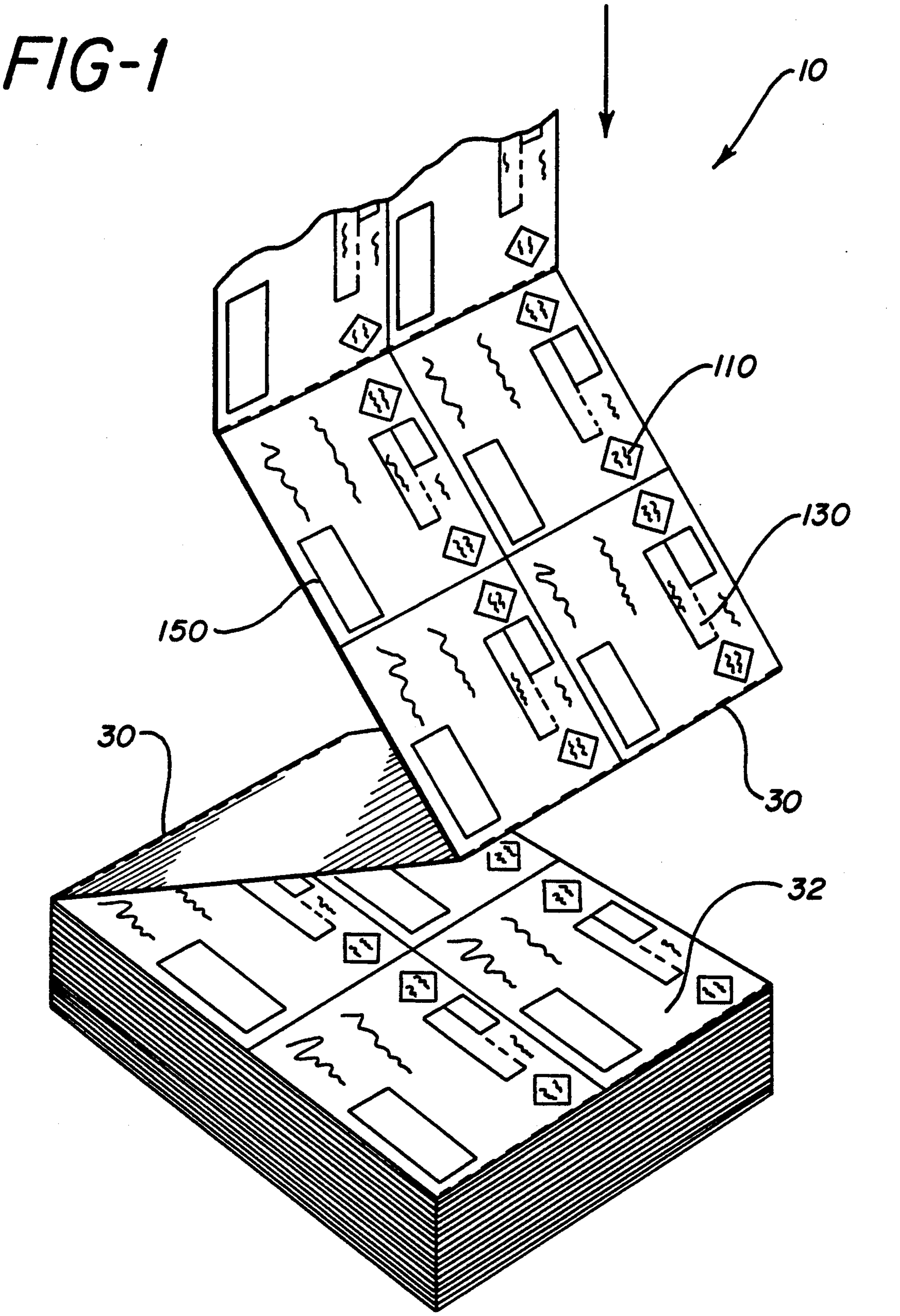
FIG. 1 is a perspective view of a continuous web of labels constructed in accordance with the present invention.

The printable label assembly 10 of the present invention is illustrated in FIG. 1 in the form of a continuous web which may be preprinted by automated equipment. Typically, nonvariable, repetitive information is printed on the web. For example, and with reference to FIG. 2, in-store price labels may be preprinted to include advertising of "special" pricing 100 or the savings 102 a customer will obtain, slogans 110, the store's name, and the like. Perforations 30 are provided transverse to the web so that the web may be folded into a zig-zag stack or separated into individual sheets of labels after the printing operation is completed.

Figure 2:
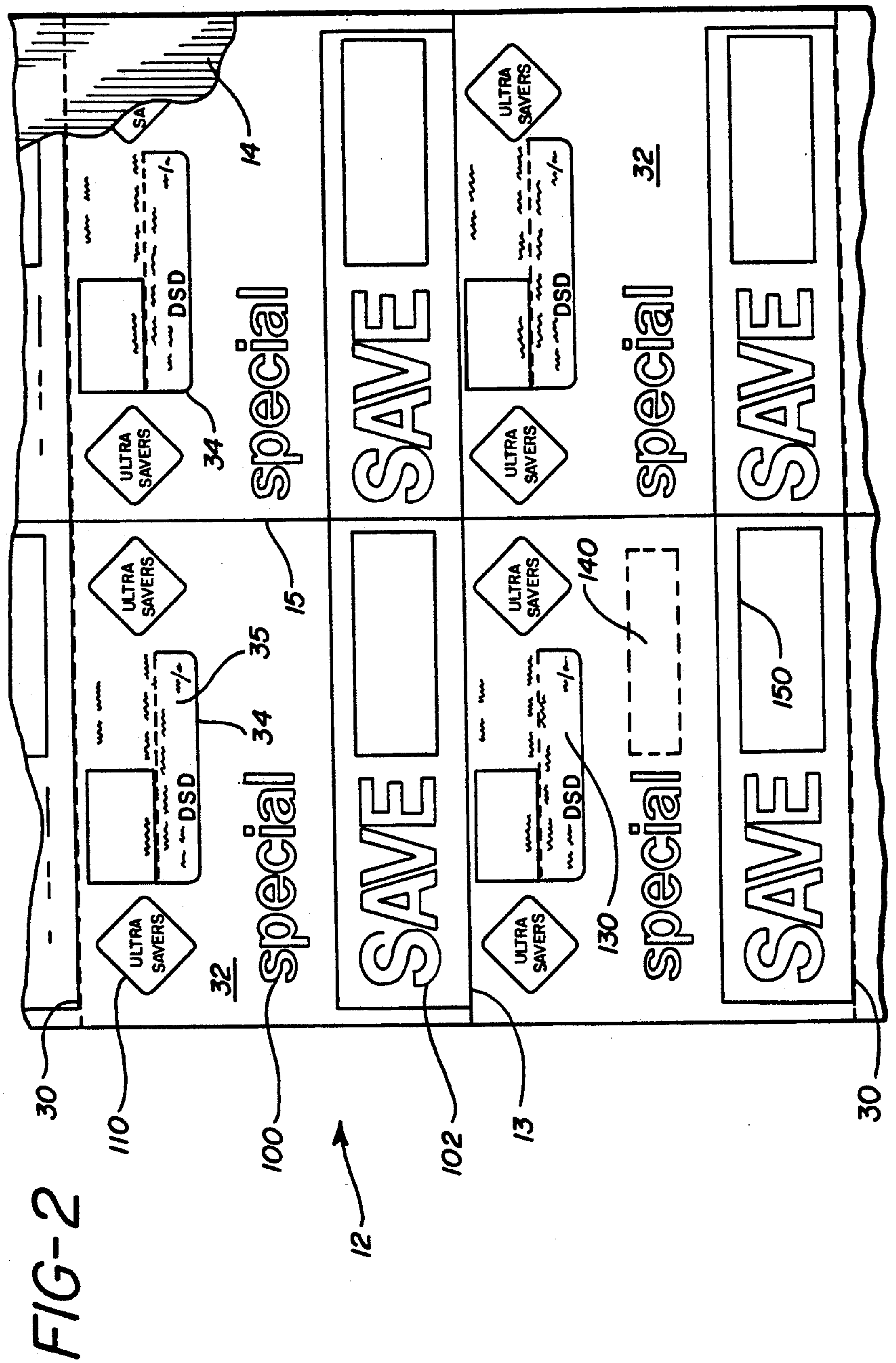
FIG. 2 is a top plan view, partially broken away, of a single sheet showing a plurality of labels.

In one form which is illustrated in FIG. 2, the continuous form for producing the label assembly includes a face sheet 12 adhered to a liner sheet 14. Face sheet 12 is die cut along lines 13 and 15 to form a plurality of labels 32. In addition, a three-sided die cut 34 which creates a flap 35 may be provided on the face sheet. In use, flap 35 may be folded inwardly and secured to a store shelf to provide a point-of-sale hang label which advertises special pricing of a product to customers. Upon removal of liner sheet 14, the area of the face sheet beneath flap 35 may contain a pressure sensitive adhesive which can be used to adhere the flap to the store shelf while the remaining portion of the label remains nontacky and hangs over the shelf as will be explained in greater detail below.

The label assembly of the present invention provides great flexibility for a customer. For many retailers, sales and pricing of products takes place on at least a weekly basis and in some instances on a daily basis. Further, advertising supplements, flyers, and media advertising must all be coordinated with in-store labels. In the past, retailers had to rely on outside printing houses to prepare all their advertising in a timely manner. If deadlines were missed, one or more aspects of the advertising campaign could not be used.

The present invention permits a retailer who is equipped only with his own laser, impact, ink jet, or thermal printer to print his own in-store, point-of-sale labels and tags for himself. As shown, for example in FIG. 2, a preprinted generic label may be customized by an end user simply by feeding the continuous web or individual sheets of labels 32 through a printer to add specific product names and pricing information. Thus, for example, unit pricing of a product may be printed in area 120, the product name may be printed in area 130, the special price may be printed in area 140, and the customer's savings over the regular product price printed in area 150. With a supply of the labels of the present invention, price changes may be effected on whatever schedule the end user desires.

While the label assembly of the present invention has been described specifically with respect to an in-store, point-of-sale hang label, those skilled in this art will appreciate the many other forms that the present invention may take. Other uses for the product label include positioning the pressure sensitive and releasable adhesives on the back of the label so that the label may be wrapped around a product with the pressure sensitive adhesive adhering to itself. The label may also be folded over onto itself to produce a two-sided label, or folded to produce a three-dimensional label which can be hung from a product or anywhere in a store. Other uses for the label assembly of the invention will become apparent from an understanding of the other embodiments discussed below.

Figure 3:
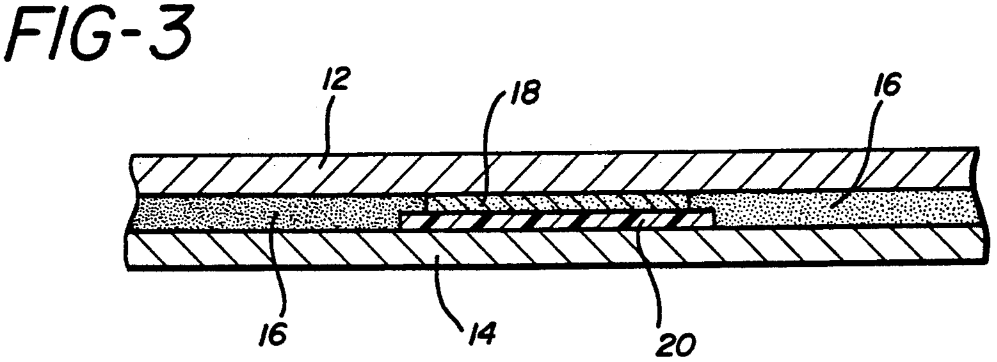
FIG. 3 is a fragmentary sectional view of one embodiment of the label assembly of the present invention.

FIG. 3 illustrates one embodiment of the label assembly 10 comprising a face sheet 12 and a removable liner sheet 14. Both face sheet 12 and liner sheet 14 are comprised of materials having printable surfaces. Suitable materials include paper or paper-like material, cardboard, card stock, and polymer sheets. However, in embodiments where the label includes an imaging capability, the face sheet should be sufficiently flexible so that when its surface is subjected to an imaging force, information may be transferred to the liner sheet.

A releasable adhesive 16 secures a first portion of the surface of face sheet 12 to a first portion of the surface of liner sheet 14 such that the face sheet and liner sheet are readily separable upon the application of a sufficient delaminating force. A suitable releasable adhesive material for use in the invention may be any adhesive which has a low cohesive strength, bonds well to paper or plastic, and is nontacky to the touch when dry. The adhesive may be applied to a surface of the face sheet or liner sheet in a fluid state and then converted to a solid by heat, cooling, radiation, or a chemical reaction. Suitable classes of releasable adhesives include water based, hot melt, solvent based and so-called 100% solids adhesives. Preferred adhesives are water-based polymer latexes or hot melts such as waxes or polymeric resins such as those taught by Doll et al, U.S. Pat. No. 5,039,652, entitled Clean Release Postal Card or Mailer, the disclosure of which is incorporated herein by reference.

A pressure sensitive adhesive 18 secures a second portion of the surface of face sheet 12 to a second portion of the surface of liner sheet 14. Pressure sensitive adhesive 18 may comprise any commercially available adhesive which has sufficient tack to laminate the face and liner sheets together and which is also capable of releasing from a release coated surface. Suitable classes of pressure sensitive adhesives include water-based acrylic emulsions and solvent-based pressure sensitive adhesives. The pressure sensitive adhesive can be either a removable or permanent type of adhesive, depending upon the intended use of the label.

Preferably, a portion of the surface of liner sheet 14 which is substantially coextensive with pressure sensitive material 18 includes a coating of a release material 20. The release material may comprise, for example, a UV curable or heat curable silicone coating. Other release coating materials known in the art may also be used. While the release material 20 and pressure sensitive adhesive 18 may be coextensive, the area oflines sheet 14 containing the release material preferably extends beyond the area containing the pressure sensitive adhesive as illustrated in FIG. 3 to ensure proper separation of the label from the liner.

The adhesives and the release material may be coated on the face sheet or liner sheet using a variety of methods known in the art including slot extrusion, roll coating, knife coating, blade coating and flexographic printing methods. In a preferred method, both the pressure sensitive and releasable adhesives are coated on a reverse roll coater. The release coating is printed on the liner from a flexographic print tower on a coater press.

Figure 4:
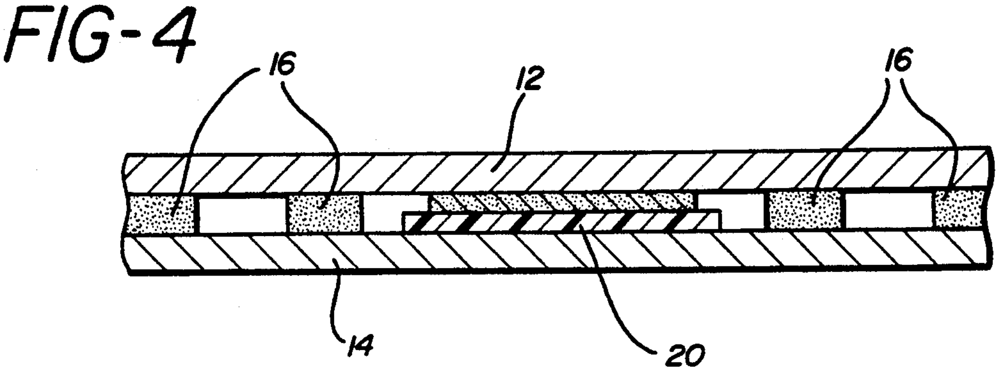
FIG. 4 is a fragmentary sectional view of another embodiment of the label assembly of the present invention.
Figure 5:
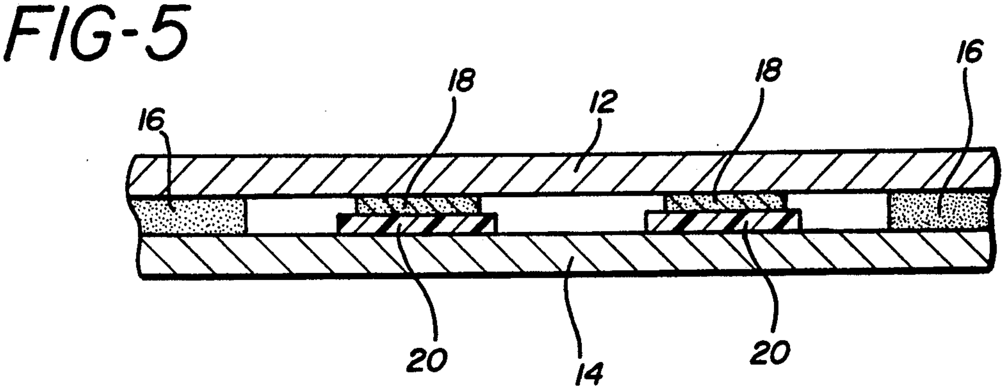
FIG. 5 is a fragmentary sectional view of another embodiment of the label assembly of the present invention.

It is not necessary that the pressure sensitive adhesive or the releasable adhesive cover the entire lower surface of the label. For example, as shown in FIG. 4 where like reference numerals identify like elements, releasable adhesive 16 may form a striped pattern on selected portions of liner sheet 14 to adhere face sheet 12 and liner sheet 14 together. In another embodiment of the invention illustrated in FIG. 5, pressure sensitive adhesive 18 may form a pattern on the lower surface of face sheet 12. The positioning and placement of releasable adhesive 16 and pressure sensitive adhesive 18 may be varied to accommodate the specific end use desired for the label or tag produced.

Figure 6:
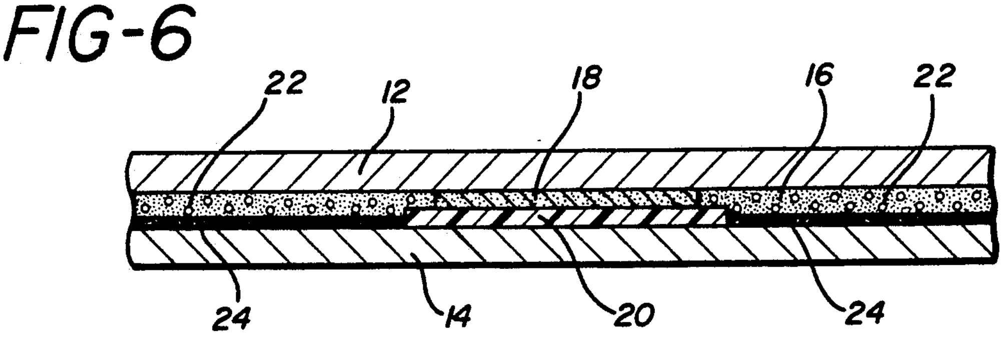
FIG. 6 is a fragmentary sectional view of another embodiment of the label assembly of the present invention.
Figure 7:
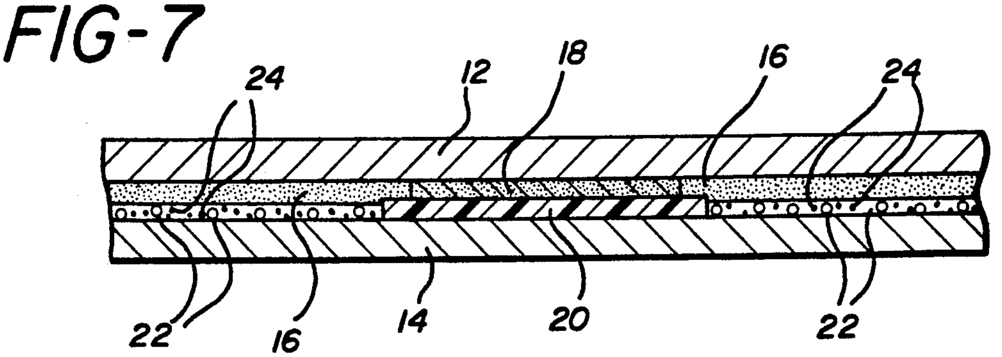
FIG. 7 is a fragmentary sectional view of another embodiment of the label assembly of the present invention.
Figure 8:
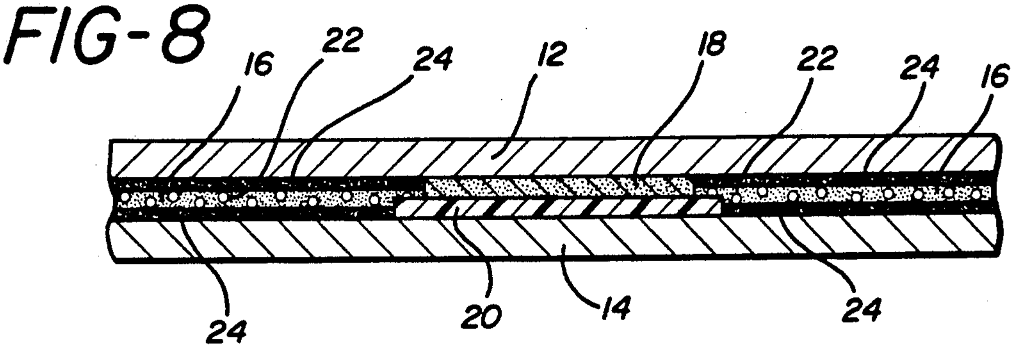

Referring now to FIGS. 6–8, additional embodiments of the invention are illustrated in which the releasable adhesive contains carbonless copy components including a color former composition 22 which, when exposed to a color developer composition 24, forms a distinctive color. These embodiments of the invention are useful in situations where it is desired to produce a duplicate record of the information printed onto a top sheet of a tag or label construction. In these embodiments, an impact-type printing device should be used. Again, the positioning of the releasable adhesive 16 and pressure sensitive adhesive 18 between the face and liner sheets may be varied by selective coating to produce the desired pattern of adhesives.

Preferably, one or both of the color former and color developer compositions is encapsulated to isolate the reactants from each other. Upon the application of an imaging force to face sheet 12, the capsules containing one of the reactants is ruptured, and the two compositions are brought together in the area beneath the imaging force to form a colored image on liner sheet 14 identical to the one made on face sheet 12 in those areas of liner sheet 14 which are coated with the color developer composition. Thus, when information is added to face sheet 12 such as, for example, in the form of product information, this information appears in duplicate form on the liner sheet by the reaction of the color forming compositions.

As shown in FIG. 6, releasable adhesive 16 contains encapsulated color former composition 22. The color former composition may be any of the several known color formers such as leuco dyes and the like. Liner sheet 14 has a color developer composition 24 coated on its surface. As described previously, either or both of the compositions may be encapsulated. Further, while the invention has been described using an encapsulated color former composition in releasable adhesive 16 and a color developer coated onto the surface of liner sheet 14, it will be apparent to those skilled in this art that the relative positioning of the compositions may be reversed, or that the encapsulated color former may be coated onto liner sheet 14 to form a self-contained carbonless sheet.

In another embodiment of the invention illustrated in FIG. 7, color developer composition 24 is blended with encapsulated color former composition 22 and coated on at least a portion of the surface of liner sheet 14. Upon the application of an imaging force to face sheet 12, the color former composition is exposed to the color developer composition, and a distinctive color is formed within the self-contained coating on the surface of liner sheet 14. In an alternative embodiment illustrated in FIG. 8, color developer composition 24 is coated on both the upper surface of liner sheet 14 and the lower surface of face sheet 12 and microcapsules of color former 22 are dispersed in releasable adhesive 16 so that a distinctive color is formed on both the face sheet and liner sheet.

FIG. 9 shows yet another embodiment of the invention in which a nontacky tag or label may be produced without the use of a releasable adhesive. Face sheet 12 is coated in a predetermined pattern over its lower surface with release material 20. The upper surface of liner sheet 14 is also coated in a different pattern with release material 20. Pressure sensitive adhesive 18 is applied over all or a portion of one of these surfaces, and the surfaces of the liner and face sheet are laminated together. When the face sheet 12 and liner sheet 14 are separated, some areas of face sheet 12 are free of pressure sensitive adhesive and are non-tacky, while other areas have pressure sensitive adhesive for attachment to other surfaces. Some areas may be free of both release material and pressure sensitive adhesive such as area 19.

In another alternative embodiment of the invention illustrated in FIG. 10, both the face sheet 12 and liner sheet 14 have printable outer surfaces. Pressure sensitive adhesive 18 secures a first portion of the surface of face sheet 12 to a first portion of the surface of liner sheet 14. A second portion of the surface of face sheet 12 and liner sheet 14 is coated with release material 20. As is shown, the portion of face sheet 12 coated with release material 20 is laminated to the portion of liner sheet 14 coated with pressure sensitive adhesive 18, and the portion of face sheet 12 coated with pressure sensitive adhesive 18 is laminated to the portion of liner sheet 14 which is coated with release material 20. Both the liner sheet and the face sheet in this embodiment are formed from the same or similar printable materials such as card stock and may be printed by the end user in two passes with variable information. Preferably, the face and liner sheets are die cut along lines 13 and 15 in an alternating offset pattern. Peeling away the portions of the face and liner forms respective pairs of labels, each having a selected portion including the pressure sensitive adhesive for adhering the labels to a substrate and each having a portion with a nontacky back. This embodiment of the invention eliminates any waste because the liner sheet is also used.

As described above, in practice, the product label assembly of the present invention is preferably preprinted with product information while on a continuous web. Die cutting of the face sheet may also be accomplished at that time, with the die cut matrix surrounding individual labels either being stripped away at that time or being allowed to remain on the liner sheet as the label is removed by an end user. Variable information, such as advertised specials, specific product names, or pricing information may then be added on site by the end user. As information regarding product pricing is time sensitive for many retailers, the invention provides the advantage of being able to add variable information on site which previously had to be sent outside for printing. Further, the labels may be printed in individual sheets or on continuous forms with a continuous liner, thus eliminating the problems of premature label separation or printing jams which have plagued prior art labels.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A printable product label assembly having a selectably adhesive portion comprising a liner sheet, a printable face sheet overlying said liner sheet, a nontacky releasable adhesive securing a first portion of a surface of said face sheet to a first portion of a surface of said liner sheet such that the surfaces of said face sheet and said inner sheet are readily separable and nontacky upon the application of an effective delaminating force, a pressure sensitive adhesive securing a second portion of said surface of said face sheet to a second portion of said surface of said liner sheet, and wherein a portion of said surface of said inner sheet which is substantially coextensive with said pressure sensitive material includes a coating of a release material.

2. The product label assembly of claim 1 wherein the portions of said liner and face sheets which are secured together by said releasable adhesive and said pressure sensitive adhesive are non-coextensive.

3. The product label assembly of claim 1 wherein said releasable adhesive forms a pattern on selected portions of said liner sheet.

4. The product label assembly of claim 1 wherein said pressure sensitive adhesive forms a pattern on selected portions of said face sheet.

5. The product label assembly of claim 1 wherein means for forming an image on either or both surfaces of said liner sheet and said face sheet are contained in the interface between said liner sheet and said face sheet.

6. The product label assembly of claim 5 wherein said means for forming an image comprise a color former composition which, when exposed to a color developer composition, forms a distinctive color, at least one of said compositions being contained in a plurality of capsules which rupture upon the application of an imaging force on said face sheet, said liner sheet having on said surface thereof said color developer composition.

7. The product label assembly of claim 5 wherein said means for forming an image comprise a color former composition on said surface of said liner sheet which, when exposed to a color developer composition, forms a distinctive color, at least one of said compositions being contained in a plurality of capsules which rupture upon the application of an imaging force on said face sheet, said color developer composition being blended with said color former composition and coated on said surface of said liner sheet.

8. The product label assembly of claim 5 wherein said means for forming an image comprise a color former composition which, when exposed to a color developer composition, forms a distinctive color, at least one of said compositions being contained in a plurality of capsules which rupture upon the application of an imaging force on said face sheet, said color developer composition being coated on either or both surfaces of said liner sheet and said face sheet.

9. The product label assembly of claim 1 wherein said face sheet is die cut to form a plurality of labels.

10. The product label assembly of claim 1 in which said assembly comprises a continuous web of labels defined by perforation lines, said web being folded zigzag into a stack.

* * * * *